(12) United States Patent
Torro et al.

(10) Patent No.: US 11,747,325 B2
(45) Date of Patent: Sep. 5, 2023

(54) BLEOMYCIN FOR MIMICKING THE EFFECT OF IONIZING RADIATIONS ON T CELLS

(71) Applicant: Novagray, Castelnau-le-Lez (FR)

(72) Inventors: Adeline Torro, Aumelas (FR); Clémence Franc, Orléans (FR)

(73) Assignee: NOVAGRAY, Castelnau-le-Lez (FR)

( * ) Notice: Subject to any disclaimer, the term of this patent is extended or adjusted under 35 U.S.C. 154(b) by 225 days.

(21) Appl. No.: 15/734,327

(22) PCT Filed: Jun. 7, 2019

(86) PCT No.: PCT/EP2019/064972
§ 371 (c)(1),
(2) Date: Dec. 2, 2020

(87) PCT Pub. No.: WO2019/234229
PCT Pub. Date: Dec. 12, 2019

(65) Prior Publication Data
US 2021/0223228 A1  Jul. 22, 2021

(30) Foreign Application Priority Data
Jun. 8, 2018 (EP) .................................. 18305698

(51) Int. Cl.
*A61K 45/00* (2006.01)
*G01N 33/50* (2006.01)
*G01N 33/68* (2006.01)

(52) U.S. Cl.
CPC ..... *G01N 33/5005* (2013.01); *G01N 33/6893* (2013.01); *G01N 2800/40* (2013.01); *G01N 2800/56* (2013.01); *G01N 2800/7004* (2013.01)

(58) Field of Classification Search
CPC ....... G01N 2800/50; G01N 2800/7004; G01N 2800/40; G01N 33/505; G01N 33/574; G01N 2800/60; G01N 33/6893; A61N 5/00
See application file for complete search history.

(56) References Cited

FOREIGN PATENT DOCUMENTS

WO  WO-2014154854 A1  10/2014

OTHER PUBLICATIONS

Blomgren et al., Effect of Bleomycin on Peripheral Lymphocytes, Acta Radiologica: Therapy, Physics, Biology, vol. 16, p. 325-336. (Year: 1977).*
Adema et al., *Comparison of bleomycin and radiation in the G2 assay of chromatid breaks*, 79 (8) Int. J. Radial. Biol. 655-661 (Aug. 2003).
Azria et al., *Radiation-induced sequelae: toward an individual profile*, 12 Cancer/Radiothérapie 619-624 (2008).
Ozsahin et al., *CD4 and CD8 T-Lymphocyte Apoptosis Can Predict Radation-Induced Late Toxicity: A Prospective Study in 399 Patients*, 11 (20) Clinical Cancer Research 7426-7433 (Oct. 15, 2005).
Tedeschi et al., *Aphidicolin and bleomycin induced chromosome damage as biomarker of mutagen sensitivity: a twin study*, 546 Mutation Research 55-64 (2004).
Weng et al., *Differential DNA damage induced by $H_2O_2$ and bleomycin in subpopulations of human white blood cells*, 652 Mutation Research 46-53 (2008).
Cloos et al., *A comparison of bleomycin-induced damage in lymphocytes and primary oral fibroblasts and keratinocytes in 30 subjects*, 14(1) Mutagenesis 87-93 (1999).
Kennedy et al., *The radiomimetic enediyne C-1027 induces unusual DNA damage responses to double strand breaks*, 45(11) Biochemistry 3747-3754 (Mar. 21, 2006).

* cited by examiner

*Primary Examiner* — Taeyoon Kim
*Assistant Examiner* — Tiffany M Gough
(74) *Attorney, Agent, or Firm* — Panitch Schwarze Belisario & Nadel LLP; Erin M. Dunston

(57) ABSTRACT

The present invention relates to a method for mimicking the effects of ionizing radiations on cells, wherein cells are contacted with bleomycin.

14 Claims, No Drawings

BLEOMYCIN FOR MIMICKING THE EFFECT OF IONIZING RADIATIONS ON T CELLS

CROSS-REFERENCE TO RELATED APPLICATIONS

This application is a U.S. National Stage Application pursuant to 35 U.S.C. § 371 of International Patent Application PCT/EP2019/064972, filed on Jun. 7, 2019, and published as WO 2019/234229 on Dec. 12, 2019, which claims priority to European Patent Application 18305698.5, filed on Jun. 8, 2018, all of which are incorporated herein by reference in their entireties for all purposes.

FIELD OF INVENTION

The present invention relates to the determination of the effects of ionizing radiations on cells, in particular on lymphocytes. More specifically, the present invention relates to a method for mimicking the effects of ionizing radiations on cells, without the use of ionizing radiations. The method of the invention may in particular be useful for assessing the individual radiosensitivity of a subject prior to a ionizing radiation treatment/radiotherapy treatment.

BACKGROUND OF INVENTION

Treatment by ionizing radiation is one of the leading treatment modalities in oncology, and over 50% of patients diagnosed with cancer undergo a treatment by ionizing radiation during their course of treatment. Although treatment by ionizing radiation is primarily a local treatment, patients are exposed to a risk of toxicities in the treatment field, and in particular in tissues surrounding the tumor, which may develop acutely (i.e., in the first 3 months) or late (i.e., more than 3 months following the treatment). Severe acute toxicities may have late consequences as recovering may be incomplete. In addition, late toxicities may occur over time and often persist with significant negative impact on quality of life among cancer survivors.

A number of factors are known to increase the risk of radiation-induced toxicity, including individual radiosensitivity (Azria, Betz et al. 2012). While toxicity risks for populations of patients are known, the determination of an individual's normal tissue radiosensitivity is seldom possible before treatment. Therefore, current practice standards commonly prescribe radiation dose according to clinical scenarios from standard recommendations, without regard to the genotype or phenotype of the individual being irradiated.

Previously, a radiosensitivity diagnostic test was developed, based on flow cytometric assessment of RILA (radiation-induced T-lymphocytes apoptosis). This diagnostic test was described as having a clear potential for selecting individuals likely to display an increased probability of toxicity to treatment by ionizing radiation (Ozsahin, Crompton et al. 2005).

However, the RILA test involves a step of treating cells with ionizing radiations. Therefore, the RILA test may not be implemented easily and routinely in standard medical analysis laboratories that are not equipped with cell irradiators, nor authorized to use such devices.

WO 2014/154854 discloses an in vitro method for mimicking the effect of ionizing radiations on T cells (T lymphocytes), comprising contacting said T cells with a radiomimetic agent such as bleomycin, but doesn't disclose or suggest the durations as herein disclosed.

Ozsahin et al (Clin Cancer Res. 2005 Oct. 15; 11(20): 7426-33) disclose that radiation-induced T-lymphocyte apoptosis can significantly predict differences in late toxicity between individuals and could be used as a rapid screen for hypersensitive patients to radiotherapy Weng et al (Mutat Res. 2008 Mar. 29; 652(1):46-53) characterize the differential sensitivities of various subpopulations of human white blood cells after exposure to H2O2 (an oxidant agent) and bleomycin (a radiomimetic glycopeptide), in vitro by measurement of induced and basal DNA damage.

Adema et al (Int J Radiat Biol. 2003 August; 79(8):655-61) indicate that bleomycin and radiation give the same sensitivity phenotypes in the G2 assay of chromatid breaks (that could be considered as a marker of radiosensitivity-predisposing genes that respond to DNA damage). However, this test is different from the RILA as described above and the duration of exposure of the cells to bleomycin is different from the one herein described.

Tedeschi et al (Mutat Res. 2004 Feb. 26; 546(1-2):55-64) describe some kind of genetic basis in the individual expression of induced chromosome damage following induction in cultured human lymphocytes by in vitro treatments with aphidicolin (APC) and bleomycin (BLM). Duration of exposure to bleomycin is different from the one herein disclosed.

Azria et al (Cancer Radiother. 2008 November; 12(6-7): 619-24) disclose that Recently low percentage of CD4 and CD8 lymphocyte apoptosis correlate with high grade of sequelae and that patients with severe radiation-induced late side effects possess four or more SNP in candidate genes (ATM, SOD2, TGFB1, XRCC1 et XRCC3) and low radiation-induced CD8 lymphocyte apoptosis in vitro.

All these documents show that bleomycine can be used, in certain conditions, to generate the same kind of DNA breaks than some radiation. However, these documents are silent as to the capacity of bleomycin to mimic the radiations conditions used for RILA, and as to whether an in vitro test can be generated to be able to replace RILA.

Thus, in particular in the field of RILA, there is a need for methods for mimicking the effect of a ionizing radiation, without the use of an irradiator (for safety or reglementary reasons).

Therefore, there is an important need to develop an alternative to the RILA test without irradiation step.

The Applicant herein provides such an alternative method, wherein cells are contacted for a specific time period at a specific concentration of bleomycin.

SUMMARY

The present invention relates to an in vitro method for mimicking the effect of a ionizing radiation on T cells, comprising contacting said T cells with at least one radiomimetic agent, preferably bleomycin, for a period of time of at least 50 hours.

In one embodiment, the concentration of said at least one radiomimetic agent, preferably bleomycin, ranges from about 100 to about 300 µg/ml.

In one embodiment, said method mimics the effect of a ionizing radiation at a dose ranging from about 2 to about 10 Gy, preferably from about 6 to about 10 Gy, more preferably of about 8 Gy.

In one embodiment, said effect is the percentage of apoptosis of lymphocytes observed 48 hours after irradiation.

In one embodiment, the dose of said at least one radiomimetic agent, preferably bleomycin, is determined using the following mathematic formula $$\tilde{x}^{co} = \frac{\hat{\beta}_0 + x^{ir}\hat{\beta}_1 - \hat{\alpha}_0}{\hat{\alpha}_1}$$

wherein ($\tilde{x}^{co}$) is the dose of compound to be applied for mimicking the effect of a specific irradiation dose ($x^{ir}$), $\hat{\beta}_0$ corresponds to an apoptosis average value for irradiation level at zero, $\hat{\beta}_1$ corresponds to the slope, i.e., to the increase of apoptosis for each 1 Gy increase, $\hat{\alpha}_0$ corresponds to the apoptosis average value for bleomycin concentration at zero and $\hat{\alpha}_1$ corresponds to the slope, i.e., to the increase of apoptosis for each 1 µg/ml increase.

In one embodiment, said T cells are contacted with bleomycin at a temperature of about 37° C. and in the presence of about 5% $CO_2$.

In one embodiment, said T cells are $CD8^+$ T cells.

In one embodiment, said T cells are comprised in a T cell containing sample selected from a blood sample, or a sample recovered from bone marrow, lymph node tissue, cord blood, thymus tissue, tissue from a site of infection, ascites, pleural effusion, spleen tissue, and tumors, preferably said T cell containing sample is a blood sample, more preferably said T cell containing sample is a whole blood sample.

In one embodiment, said method is a method for determining the individual radiosensitivity of a subject, and comprises contacting a T cell containing sample previously obtained from the subject with at least one radiomimetic agent, preferably bleomycin for a period of time of at least 50 hours.

In one embodiment, said subject is diagnosed with cancer.

In one embodiment, said subject is treated or is planned to be treated with a ionizing radiation treatment.

In one embodiment, said method is for assessing a risk of developing side effects after a ionizing radiation treatment.

In one embodiment, said method comprises:
a. contacting a T cell containing sample previously obtained from a subject with at least one radiomimetic agent, preferably bleomycin, and
b. measuring the percentage of $CD8^+$ T cell apoptosis in the sample from the subject.

In one embodiment, said method comprises comparing the $CD8^+$ T cell apoptosis measured at step (b) with a reference $CD8^+$ T cell apoptosis.

The present invention further relates to a kit for implementing the in vitro method as described hereinabove, comprising means for measuring radiomimetic agent-induced T cell apoptosis. In one embodiment, said kit comprises at least one radiomimetic agent, preferably bleomycin, and means for measuring $CD8^+$ T cell apoptosis.

Definitions

In the present invention, the following terms have the following meanings:

The terms "a" and "an" refer to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "biochemical marker" refers to a variable that may be measured in a sample from the subject, said sample being preferably a blood sample.

The term "Cox regression" refers to a usual statistical model for time-to-event analysis (Cox, et al. 1984). Apart from a classification algorithm which directly deals with binary or multi-class outcomes, Cox regression defines a semi-parametric model to directly relate the predictive variables with the real outcome, which may be, for example, a survival time (e.g., in months or years) or a time without occurrence of side effects or recurrence of a disease. Multivariate Cox function is considered as the best hazard function in terms of discrimination for time-to-event endpoint to combine independent parameters.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene, or cDNA, produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" refers to the transcription and/or translation of a particular nucleotide sequence driven by a promoter.

The term "instructional material" includes a publication, a recording, a diagram, or any other medium of expression which can be used to communicate the usefulness of the kit of the invention. The instructional material of the kit of the invention may, for example, be affixed to a container which contains the reagents for implementing the method of the invention or be shipped together with a container which contains the reagents for implementing the method of the invention. Alternatively, the instructional material may be shipped separately from the container with the intention that the instructional material be used cooperatively by the recipient.

The term "in vitro method" refers to a method comprising steps performed in vitro (e.g., a measurement of apoptosis) or ex-vivo (e.g., multivariate cox regression model obtained with apoptosis percentage, clinical parameters or biochemical marker previously evaluated on patients).

The term "non-invasive", when referring to a method according to the present invention, means that the method of the invention does not comprise obtaining a tissue sample from the body of a subject. In one embodiment, a blood sample is not considered as a tissue sample.

"ROC" In statistics, a receiver operating characteristic (ROC), or ROC curve, is a graphical plot that illustrates the performance of a binary classifier system as its discrimination threshold is varied. The curve is created by plotting the sensitivity against the specificity (usually 1−specificity) at successive values from 0 to 1.

"AUROC" stands for area under the ROC curve, and is an indicator of the accuracy of a prognostic or diagnostic test. ROC curve and AUROC are well-known in the field of statistics.

The term "sensitivity (Se) of a method of prognosis" refers to the proportion of patients with a risk to develop side-effect that are correctly identified as such using a method of prognosis.

The term "specificity (Sp) of a method of prognosis" refers to a measure of the proportion of patients without risk to develop side-effect that are correctly identified as such using a method of prognosis.

The term "side effect" (or adverse event) refers to an unfavorable and unintended sign (including an abnormal laboratory finding), symptom or disease temporally associated with the use of a medical treatment. In particular, a ionizing radiation-induced side effect is a side effect induced in a subject by a ionizing radiation treatment. Severity of side effects may be defined according to the Common Terminology Criteria for Adverse Events (CTCAE, e.g., CTCAE v3.0 or CTCAE v4.0 or CTCAE v5.0). According to the CTCAE, globally the following grades of side effects may be distinguished: Grade 1: mild side effect, Grade 2: moderate side effect, Grade 3: severe side effect, Grade 4: life threatening or disabling side effect and Grade 5: death related to side effect, but specifically defined for each symptom. In one embodiment of the invention, the side effect is at least a Grade 2 side effect. In one embodiment, the side effect is a Grade 2, 3, 4 or 5 side-effects, preferably a Grade 2, 3 or 4 side-effects.

The term "subject" is intended to include any living organisms (e.g., mammals, preferably humans). In one embodiment, a subject is a "patient", i.e., a warm-blooded animal, preferably a human, who/which is awaiting the receipt of, or is receiving medical care or was/is/will be the object of a medical procedure, or is monitored for the development of the targeted disease or condition. In one embodiment, the subject is an adult (for example a subject above the age of 18). In another embodiment, the subject is a child (for example a subject below the age of 18). In one embodiment, the subject is a male. In another embodiment, the subject is a female.

The terms "treat", "treatment" and "treating" refer to the reduction or amelioration of the progression, severity and/or duration of a targeted disease (e.g., cancer), or to the amelioration of one or more symptoms (preferably, one or more discernible symptoms) of a targeted disease, wherein said amelioration results from the administration of one or more therapies. In one embodiment the terms "treat", "treatment" and "treating" refer to the inhibition of the progression of a targeted disease, either physically by, e.g., stabilization of at least one discernible symptom, physiologically by, e.g., stabilization of a physical parameter, or both. In other embodiments the terms "treat", "treatment" and "treating" refer to the reduction or amelioration of the progression, severity and/or duration of a targeted disease, or to the amelioration of one or more symptoms of a targeted disease. A subject is successfully "treated" for a disease if, after receiving a therapeutically effective amount of a therapeutic agent or treatment, the subject shows observable and/or measurable reduction in the number of pathogenic cells or reduction in the percent of total cells that are pathogenic; relief to some extent of one or more of the symptoms associated with the specific disease; reduced morbidity and mortality, and/or improvement in quality of life issues. The above parameters for assessing successful treatment and improvement in the condition are readily measurable by routine procedures familiar to a physician.

DETAILED DESCRIPTION

The present invention first relates to an in vitro method for mimicking the effect of a ionizing radiation on T lymphocytes, comprising contacting said T lymphocytes with at least one radiomimetic agent.

The term "radiomimetic agent" as used here refers to a substance that produces effects on living cells that are similar to those provoked by ionizing radiation.

In one embodiment, the at least one radiomimetic agent is selected from the group comprising, but not limited to, bleomycin, streptonigrin, aphidicolin, enediyne antibiotics, and hydrogen peroxide.

In one embodiment, the at least one radiomimetic agent is bleomycin, such as, for example, bleomycin solubilized in ethanol, water or DMSO. Preferably, bleomycin is in an aqueous solvent. Examples of salts of bleomycin that may be used in the present invention include, but are not limited to, bleomycin sulfate or bleomycin hydrochloride.

In one embodiment, bleomycin used in the present invention is bleomycin sulfate, preferably in an aqueous solvent. Bleomycin is commercially available. Examples of bleomycin formulations that may be used include, without limitation, bleomycin provided by Euromedex or by Interchim.

In one embodiment, the T cells are $CD4^+$ or $CD8^+$ T cells, preferably $CD8^+$ T cells.

In one embodiment, the T cells of the invention are contained in a T cell containing sample, or are recovered from a T cell containing sample.

Examples of T cell containing samples include, but are not limited to, whole blood samples and samples recovered from bone marrow, lymph node tissue, cord blood, thymus tissue, tissue from a site of infection, ascites, pleural effusion, spleen tissue, and tumors. Other T cell containing samples can be used in the method herein disclosed, such as an extract containing predominantly PBMC (peripheral blood mononuclear cells) or isolated T cells (in particular isolated CD8 T cells). Predominantly is intended to indicate that at least 80%, more preferably at least 90% more preferably at least 95% of the cells present in the extract are of the indicated cell type.

In one embodiment, the T lymphocyte containing sample can be obtained from a unit of blood collected from a subject using any number of techniques known to the skilled artisan, such as, for example, by leukapheresis.

In one embodiment, said sample is a bodily fluid sample, such as, for example, a blood, plasma, serum, lymph, urine, cerebrospinal fluid or sweat sample.

In one embodiment, said sample is a blood sample.

In one embodiment, the sample is recovered prior to the implementation of the method of the invention, i.e., the step of recovering the sample is not part of the method of the invention.

In one embodiment, the T cell containing sample (preferably blood sample) is collected from a subject in a heparinized tube.

In one embodiment, the T cell containing sample is freshly recovered. In one embodiment, the T cell containing sample is preserved at room temperature (preferably from about 18° C. to about 25° C.) in a heparinized tube.

In another embodiment, the T cell containing sample is cryopreserved (i.e., frozen in liquid nitrogen) and thawed.

In one embodiment, the T cells are cultured in a cell culture medium prior to the contact with the at least one radiomimetic agent. Examples of cell culture medium that may be used include, but are not limited to, RPMI-1640 (Thermofisher, France) and DMEM (Dulbecco Modified Eagle Medium, Thermofisher). In one embodiment, the cell culture medium is optionally supplemented with 20% fetal calf serum (FCS) (e.g., FCS provided by EuroBio, France). In one embodiment, the T cells are maintained at 37° C. with 5% $CO_2$.

In one embodiment, the at least one radiomimetic agent is added to the culture medium.

In one embodiment, the T cells are contacted with the at least one radiomimetic agent for at least about 50 hours, at least about 51, 52, 53, 54, 55, 56, 57, 58, 59, 60, 61, 62, 63, 64, 65, 66, 67, 68, 69, 70, 71, 72, 73, 74, 75, 76, 77, 78, 79 or at least about 80 hours.

In one embodiment, the T cells are contacted with the at least one radiomimetic agent for about 50 hours, about 51, 52, 53, 54, 55, 56, 57, 58, 59, 60, 61, 62, 63, 64, 65, 66, 67, 68, 69, 70, 71, 72, 73, 74, 75, 76, 77, 78, 79 or about 80 hours.

Indeed, the Applicant has demonstrated that, surprisingly, contacting the T cells with the at least one radiomimetic agent in conditions mimicking the RILA test, i.e., after 24 hours of cell culture and for a total duration of about 48 hours, is not sufficient to reproduce the effect of ionizing radiation on T cells (in particular to obtain the same apoptosis level in the CD8 lymphocytes as obtained according to the RILA procedure, and in particular when 8 Gy are applied to the cells cultured for 24 hours, and apoptosis is looked at 48 hours after irradiation). Willing to mimic the effect of ionizing radiation on T cells, the Applicant further surprisingly demonstrated that a longer contacting step, such as, for example for a period of time ranging from about 50 hours to about 80 hours, allows reproducing the effect of ionizing radiation on T cells. In particular, the at least one radiomimetic agent can be added at the start of the cell culture and maintained in the medium for at least 50 hours. Advantageously, it is maintained for at least 60 hours, or for at least or about 72 hours or for at least or about 75 hours, or for between about 70 and 77 hours. It is postulated that the apoptosis induction is complex and takes some time, which is why a longer time of exposition of the cells to the radiomimetic agent is required, even though some markers of radiation (such as DNA breaks) are present in the cells early after the cells are exposed to the radiomimetic agent.

In one embodiment, the T cells are contacted with the at least one radiomimetic agent at about 37° C. with about 5% $CO_2$.

In one embodiment, T cells are added in a cell culture medium containing the at least one radiomimetic agent. In another embodiment, the at least one radiomimetic agent is added to a culture medium previously containing the T cells.

In one embodiment, the in vitro method of the invention is for mimicking the effect on T lymphocytes of a ionizing radiation ranging from about 2 Gray (Gy) to about 10 Gy, preferably from about 5 to about 9 Gy, more preferably from about 6 to about 10 Gy, such as, for example, a ionizing radiation of about 6 Gy, about 8 Gy or about 10 Gy.

The skilled artisan would easily understand that the dose of the at least one radiomimetic agent to be used depend on the ionizing radiation dose to be mimicked.

In one embodiment, said dose is determined according to the following mathematic formula:

$$\tilde{x}^{co} = \frac{\hat{\beta}_0 + x^{ir}\hat{\beta}_1 - \hat{\alpha}_0}{\hat{\alpha}_1}$$

wherein $\tilde{x}^{co}$ is the dose of compound to be applied for mimicking the effect of a specific irradiation dose ($x^{ir}$), $\hat{\beta}_0$ corresponds to an apoptosis average value for irradiation level at zero, $\hat{\beta}_1$ corresponds to the slope, i.e., to the increase of apoptosis for each 1 Gy increase, $\hat{\alpha}_0$ corresponds to the apoptosis average value for bleomycin concentration at zero and $\hat{\alpha}_1$ corresponds to the slope, i.e., to the increase of apoptosis for each 1 µg/mL increase.

In one embodiment, $\hat{\beta}_0$ ranges from about 10 to about 20, preferably is of about 14 to 18. In one embodiment, $\hat{\beta}_1$ ranges from about 0.5 to about 2, preferably from about 0.75 to about 1.25. In one embodiment, $\hat{\alpha}_0$ ranges from about 7.5 to about 20, preferably from about 10 to about 15. In one embodiment, $\hat{\alpha}_1$ ranges from about 0.03 to about 0.15, preferably from about 0.05 to about 0.1.

In one embodiment, the concentration of the at least one radiomimetic agent ranges from about 50 µg/ml to about 500 µg/ml, preferably from about 100 µg/ml to about 300 µg/ml, such as, for example, about 100, 125, 150, 175, 200, 225, 250, 275, or 300 µg/ml.

In one embodiment, the at least one radiomimetic agent is bleomycin and the concentration of bleomycin is ranging from about 50 µg/ml to about 500 µg/ml, preferably from about 100 µg/ml to about 300 µg/ml, such as, for example, about 100, 125, 150, 175, 200, 225, 250, 275, or 300 µg/ml.

In one embodiment, the method of the invention is for mimicking the effect of a 6 Gy irradiation, and the concentration of the at least one radiomimetic agent (preferably of bleomycin) ranges from about 50 µg/ml to about 500 µg/ml, preferably from about 100 µg/ml to about 300 µg/ml, such as, for example, about 100, 125, 150, 175, 200, 225, 250, 275, or 300 µg/ml.

In one embodiment, the method of the invention is for mimicking the effect of a 8 Gy irradiation, and the concentration of the at least one radiomimetic agent (preferably of bleomycin) ranges from about 50 µg/ml to about 500 µg/ml, preferably from about 100 µg/ml to about 300 µg/ml, such as, for example, about 100, 125, 150, 175, 200, 225, 250, 275, or 300 µg/ml. In one embodiment, the method of the invention is for mimicking the effect of a 8 Gy irradiation, and the concentration of the at least one radiomimetic agent (preferably of bleomycin) ranges from about 135 to about 160 µg/mL.

In one embodiment, the method of the invention is for mimicking the effect of a 10 Gy irradiation, and the concentration of the at least one radiomimetic agent (preferably of bleomycin) ranges from about 50 µg/ml to about 500 µg/ml, preferably from about 100 µg/ml to about 300 µg/ml, such as, for example, about 100, 125, 150, 175, 200, 225, 250, 275, or 300 µg/ml.

In one embodiment, the method of the invention comprises:
  a) contacting T cells with at least one radiomimetic agent, and
  b) measuring radiomimetic agent-induced T-cell apoptosis.

In one embodiment, the method of the invention comprises:

a) contacting a T cell containing sample with at least one radiomimetic agent, and
b) measuring radiomimetic agent-induced T-cell apoptosis in the T cell containing sample.

In one embodiment, the in vitro method of the invention comprises measuring radiomimetic agent-induced apoptosis of CD4 and/or CD8 T-lymphocyte. In one embodiment, the method of the invention comprises measuring radiomimetic agent-induced CD8 T-lymphocyte apoptosis.

In one embodiment, at the end of the contacting step, T cells are transferred to pre-labeled centrifuge tubes, for centrifugation, such as for example, for 5 minutes at 390 g. After centrifugation, the sample may be labeled with a fluorochrome coupled-anti-CD4 and/or fluorochrome coupled-anti-CD8 antibody.

Then, in one embodiment, a lysis buffer is added to the centrifuge tube in order to lyse any non-lymphocyte cell (such as, for example, red blood cells). An example of lysis buffer is the ammonium chloride based lysing reagent provided by Beckton Dickinson (USA).

After lysis, reagents are added to the tube for evaluating lymphocytes apoptosis according to usual methods known from the person skilled in the art.

Examples of methods for measuring T-lymphocytes (preferably CD8 T-lymphocytes) apoptosis include, but are not limited to, FACS analysis (e.g., with propidium iodide and RNase A as reagents), dosage of Annexin V, and dosage of caspases. Preferably the evaluation of T lymphocytes apoptosis is carried out by FACS analysis.

In one embodiment, the method of the invention comprises the measurement of apoptosis features occurring in the cell such as, for example, membrane asymmetry (that may be visualized, for example, by the phosphatidyl serine externalization), membrane permeability, mitochondria metabolic activity, caspase activation and chromatin condensation.

Thus, in one embodiment, the apoptosis measurement step of the invention comprises the use of specific reagents to evaluate T cell apoptosis features. Examples of such reagents include, but are not limited to, propidium iodide, 7-AAD, fluorochrome coupled-annexin, YO-PRO dyes, PO-PRO dyes, Resazurin, Hoechst, fluorochrome coupled-caspase antibodies and JC-1 dye. Preferably, the method of the invention uses propidium iodide.

In one embodiment, the method of the invention comprises measuring a percentage of apoptotic cells after the contacting step.

In one embodiment, the measurement of apoptosis is carried out in triplicate.

In one embodiment, the method of the invention further comprises a step of measuring a percentage of apoptotic T cells in a control sample not contacted with the at least radiomimetic agent ("basal T cell apoptosis"). In one embodiment, for measuring basal T cell apoptosis, cells are kept in the exact same conditions than the test sample (e.g., medium, temperature, $CO_2$, etc. . . . ), except that these cells are not contacted with the at least one radiomimetic agent.

In one embodiment, the in vitro method of the invention allows determining the individual radiosensitivity of a subject.

In one embodiment, the in vitro method of the invention is thus for assessing the risk of developing side effects after ionizing radiation in a subject.

In one embodiment, the method of the invention aims at predicting the risk of developing side effects during ionizing radiation treatment and during a period of about 1, 3, 6, 12, 18, 24, 30 or 36 months after ionizing radiation treatment.

In one embodiment, the in vitro method of the invention aims at predicting the risk of developing acute side effects, i.e., side effects occurring during ionizing radiation treatment or less than about 1 week, 2 weeks, 3 weeks or 4 weeks after ionizing radiation treatment, or less than about 1, 2 or 3 months after ionizing radiation treatment.

In another embodiment, the in vitro method of the invention aims at predicting the risk of developing late side effects, i.e., side effects occurring at least about 3 months after ionizing radiation treatment, such as, for example, between about 3 months and about 6 months after ionizing radiation treatment, between about 3 months and about 12 months after ionizing radiation treatment, between about 3 months and about 18 months after ionizing radiation treatment, between about 3 months and about 2 years after ionizing radiation treatment, between about 3 months and about 30 months after ionizing radiation treatment, or between about 3 months and about 3 years after ionizing radiation treatment. In one embodiment, the late side effects occur about 4, 5, 6, 7, 8, 9, 10, 11, 12 months or more after ionizing radiation treatment, or 2 or 3 years or more after ionizing radiation treatment.

In one embodiment, the side-effects as listed hereinabove are at least Grade 2 side effects according to the CTCAE, e.g., to the v3.0 CTCAE, the v4.0 CTCAE or the v5.0 CTCAE. In one embodiment, the side-effects as listed hereinabove are Grade 2, Grade 3, Grade 4 or Grade 5 side effects according to the CTCAE, e.g., to the v3.0 CTCAE, preferably Grade 2, Grade 3, or Grade 4.

In one embodiment, the method of the invention is non-invasive.

In one embodiment, the method of the invention comprises contacting T cells previously obtained from the subject with at least one radiomimetic agent.

In one embodiment, the subject is a human.

In one embodiment, the subject is, was or will be treated by ionizing radiation.

In one embodiment, the T cells or T cell containing sample are/is obtained from the subject before the beginning of the treatment with ionizing radiation.

In one embodiment, the subject is diagnosed with a tumor. In one embodiment, the subject is diagnosed with a malignant tumor. In another embodiment, the subject is diagnosed with a non-malignant (or benign tumor). Examples of non-malignant tumor include, but are not limited to, moles, uterine fibroids, neoplasms (e.g., lipoma, chondroma, adenoma, teratoma, hamartoma and the like).

In another embodiment, the subject is diagnosed with a non-malignant disorder that may be treated by ionizing radiations. Examples of non-malignant disorders that may be treated by ionizing radiations include, but are not limited to, Graves' disease, calcaneal spur and keloids.

In one embodiment, the subject is diagnosed with cancer. Examples of cancers include, but are not limited to, prostate cancers, breast cancers, gastrointestinal cancers (e.g., colon cancer, small intestine cancer or colorectal cancer), stomach cancers, pancreas cancers, lung cancers (e.g., non-small cell lung cancer), mesothelioma, bladder cancers, kidney cancers, thyroid cancers, cardiac cancers, genitourinary tract cancers, liver cancers, bone cancers, nervous system cancers (e.g., brain cancer), gynecological cancers (e.g., ovarian cancer), testicular cancer, hematologic cancers, throat cancers, head and neck cancers, oral cancers, skin cancers, and adrenal glands cancers.

In one embodiment, said cancer is a tumor, such as, for example, a solid tumor. In another embodiment, said cancer is a blood cancer. In another embodiment, said cancer is a hematologic malignancy.

Examples of breast cancer include, but are not limited to ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, lobular carcinoma in situ, male breast cancer, Paget's disease of the nipple, phyllodes tumors of the breast and recurrent & metastatic breast cancer.

Examples of gastrointestinal cancer include, but are not limited to, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, and rectal cancers.

Examples of lung cancer include, but are not limited to, adenocarcinoma (formerly bronchioloalveolar carcinoma), undifferentiated small cell carcinoma, undifferentiated large cell carcinoma, small cell carcinoma, large cell carcinoma, large cell neuroendocrine tumors, small cell lung cancer (SCLC), undifferentiated non-small cell lung cancer, bronchial adenoma, sarcoma, lymphoma, chondromatosis hamartoma, Pancoast tumors and carcinoid tumors.

Examples of mesothelioma include, but are not limited to, pleural mesothelioma, peritoneal mesothelioma, pericardial mesothelioma, end stage mesothelioma as well as epithelioid, sarcomatous, and biphasic mesothelioma.

Examples of bladder cancer include, but are not limited to, transitional cell bladder cancer (formerly urothelial carcinoma), invasive bladder cancer, squamous cell carcinoma, adenocarcinoma, non-muscle invasive (superficial or early) bladder cancer, sarcomas, small cell cancer of the bladder and secondary bladder cancer.

Examples of cardiac cancer include, but are not limited to, sarcoma (angiosarcoma, fibrosarcoma, rhabdomyosarcoma, liposarcoma), myxoma, rhabdomyoma, fibroma, lipoma and teratoma.

Examples of genitourinary tract cancer include, but are not limited to, kidney (adenocarcinoma, Wihn's tumor [nephroblastoma], lymphoma, leukemia), bladder and urethra (squamous cell carcinoma, transitional cell carcinoma, adenocarcinoma), prostate (adenocarcinoma, sarcoma), and testis cancers (seminoma, teratoma, embryonal carcinoma, teratocarcinoma, choriocarcinoma, sarcoma, interstitial cell carcinoma, fibroma, fibroadenoma, adenomatoid tumors, lipoma).

Examples of liver cancer include, but are not limited to, hepatoma (hepatocellular carcinoma), cholangiocarcinoma, hepatoblastoma, angiosarcoma, hepatocellular adenoma, and hemangioma.

Examples of bone cancers include, but are not limited to, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors.

Examples of nervous system cancers include, but are not limited to, skull cancer (osteoma, hemangioma, granuloma, xanthoma, osteitis deformans), meninges cancer (meningioma, meningosarcoma, gliomatosis), and brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma).

Examples of gynecological cancers include, but are not limited to, uterus cancer (endometrial carcinoma), cervix cancer (cervical carcinoma, pre-tumor cervical dysplasia), ovaries cancer (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva cancer (squamous cell carcinoma, intraepithelial carcinoma, adenocarcinoma, fibrosarcoma, melanoma), and vagina cancer (clear cell carcinoma, squamous cell carcinoma, botryoid sarcoma [embryonal rhabdomyosarcoma], fallopian tubes cancer [carcinoma]).

Examples of hematologic cancers include, but are not limited to, blood cancer (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma].

Examples of skin cancers include, but are not limited to, malignant melanoma, basal cell carcinoma, squamous cell carcinoma, Karposi's sarcoma, moles dysplastic nevi, lipoma, angioma, dermatofibroma, and keloids.

Examples of adrenal glands cancers include, but are not limited to, neuroblastoma.

In one embodiment, said cancer is advanced cancer. As used herein, the term "advanced cancer" refers to a cancer that has spread to other places in the body and usually cannot be cured or controlled with treatment. In particular, locally advanced cancer is cancer that has spread from where it started to nearby tissue or lymph nodes.

In one embodiment, said cancer is an unresectable cancer. As used herein, the term "unresectable cancer" refers to a cancer that may not be removed by surgery.

In one embodiment, said cancer is a recurrent cancer. As used herein, the term "recurrent cancer" refers to a cancer that has recurred (come back). The cancer may come back to the same place as the original (primary) tumor or to another place in the body.

In one embodiment, said cancer is a metastatic cancer. As used herein, the term "metastatic cancer" refers to a cancer that has spread from the place where it first started to another place in the body. A tumor formed by metastatic cancer cells may be called a metastatic tumor or a metastasis. The metastatic tumor contains cells that are like those in the original (primary) tumor.

In one embodiment, the subject is planned to be treated by ionizing radiation, and the method of the invention is implemented before the beginning of the treatment by ionizing radiation.

The term "ionizing radiation", as used herein, refers to a treatment involving the use of radiation such as, for example, X-rays (electron or photon beams), gamma rays, or protons, to kill or damage cancer or tumor cells and stop them from growing and multiplying.

In one embodiment, the ionizing radiation involves the use of X-rays.

In one embodiment, the side effects are side effects induced by ionizing radiation in the area of the treatment, such as, for example, in the pelvic area for the treatment of prostate cancer, or in the breast area for the treatment of breast cancer.

Examples of ionizing radiation-induced side effects that may be induced during the treatment of prostate cancer include, but are not limited to, genitourinary (such as, for example, urinary and sexual toxicities), gastrointestinal and neurologic toxicities.

Examples of ionizing radiation-induced side effects that may be induced during the treatment of breast cancer include, but are not limited to, atrophic skin, telangiectasia, induration (fibrosis), necrosis or ulceration. In one embodiment, the ionizing radiation-induced side effects are breast late side effects, i.e., side effects induced during the treatment of breast cancer (e.g., atrophic skin, telangiectasia, induration (fibrosis), necrosis or ulceration) and occurring at least about 3 months after ionizing radiation treatment (such as, for example, between about 3 months and about 6 months after ionizing radiation treatment, between about 3 months and about 12 months after ionizing radiation treatment, between about 3 months and about 18 months after ionizing radiation treatment, between about 3 months and about 2 years after ionizing radiation treatment, between about 3 months and about 30 months after ionizing radiation treatment, or between about 3 months and about 3 years after ionizing radiation treatment or about 4, 5, 6, 7, 8, 9, 10, 11, 12 months or more after ionizing radiation treatment, or 2 or 3 years or more after ionizing radiation treatment).

In one embodiment, the in vitro method of the invention further comprises a step of comparing the radiomimetic agent-induced T cell with a reference radiomimetic agent-induced T cell apoptosis, thereby determining if the subject presents a high or low risk to develop ionizing radiation-induced side-effects.

In one embodiment, the reference radiomimetic agent-induced T cell apoptosis corresponds to the apoptosis measured in a reference population. In one embodiment, the reference apoptosis was measured in a reference population comprising patients (e.g., cancer patients) treated with ionizing radiation and having experienced radiation-induced side-effects during follow-up (such as, for example, during ionizing radiation and/or during the follow-up after ionizing radiation, such as, for example, 1 month, 3, 6, 12, 18, 24, 30 or 36 months after the end of the ionizing radiation). In another embodiment, the reference apoptosis was measured in a reference population comprising patients (e.g., cancer patients) treated with ionizing radiation and having experienced no ionizing radiation-induced side-effects during follow-up (such as, for example, during ionizing radiation and/or during the follow-up after ionizing radiation, such as, for example, 1 month, 3, 6, 12, 18, 24, 30 or 36 months after the end of the ionizing radiation).

A reference apoptosis can be derived from population studies, including without limitation, such subjects having similar age range, subjects in the same or similar ethnic group, similar disease history, similar ionizing radiation treatment and the like.

In one embodiment, the reference apoptosis is constructed using algorithms and other methods of statistical and structural classification.

In one embodiment, the reference apoptosis corresponds to the mean apoptosis measured in the reference population. In one embodiment of the invention, the reference apoptosis corresponds to the median apoptosis measured in the reference population.

In one embodiment, the method of the invention is computerized (or computer-implemented).

In one embodiment, the method of the invention comprises determining if the radiomimetic agent-induced T cell apoptosis is superior to the reference apoptosis, or inferior or equal to said reference apoptosis.

In another embodiment, the method of the invention comprises determining the percentile wherein the radiomimetic agent-induced T cell apoptosis measured for the subject may be positioned. According to this embodiment, the radiomimetic agent-induced T cell apoptosis values measured in a reference population are classified in percentiles, wherein the radiomimetic agent-induced T cell apoptosis values obtained for all subjects of the reference population are ranged according to their numerical value in ascending order. In one embodiment of the invention, the percentiles are percentiles of subjects, i.e., each percentile comprises the same number of subjects. Therefore, the first percentile corresponds to subjects with the lowest radiomimetic agent-induced T cell apoptosis values, while the last percentile corresponds to subjects with the highest radiomimetic agent-induced T cell apoptosis values. In one embodiment, when three percentiles are drawn, each percentile is named a tertile. In another embodiment, when four percentiles are drawn, each percentile is named a quartile. In another embodiment, when five percentiles are drawn, each percentile is named a quintile.

The skilled artisan knows how to determine the reference apoptosis or percentiles of radiomimetic agent-induced T cell apoptosis values from radiomimetic agent-induced T cell apoptosis values obtained in a reference population.

A non-limiting example of such method include the drawing of a ROC curve to determine the cut-off of radiomimetic agent-induced T cell apoptosis value measured for the subject with side effect vs subject without side effect (AUROC) which maximize Se and Sp.

In one embodiment, determining the radiomimetic agent-induced T cell apoptosis, will help the physician to adapt the dose and sequences of ionizing radiation treatment to the patient to limit the ionizing-radiation induced side effects, and optionally to adapt the treatment by replacing ionizing radiation treatment with other therapeutic treatments.

In a particular embodiment, the radiomimetic agent-induced T cell apoptosis is used to choose a suitable treatment for the patient, such as an appropriate ionizing radiation regimen.

Another object of the invention is a method for implementing an adapted patient care (or treatment) for a patient, wherein said method comprises:

assessing the risk for said patient to develop ionizing radiation-induced side-effects, using the in vitro method as described hereinabove;

implementing an adapted patient care (or treatment) depending on the risk for the patient to develop ionizing radiation-induced side-effects.

In one embodiment, the patient presents a high risk to develop ionizing radiation-induced side effects and the adapted patient care may be selected from the group comprising decreased ionizing radiation dosage regimen, or alternative treatment, such as, for example, surgery.

In one embodiment, the patient presents no or only a low risk to develop ionizing radiation-induced side effects and the adapted patient care may be selected from the group comprising increased ionizing radiation dosage regimen.

Another object of the present invention is thus a computer software for implementing the method of the invention.

In one embodiment, the in vitro method of the invention is implemented with a microprocessor comprising a software configured to calculate a radiomimetic agent-induced T cell apoptosis.

Another object of the present invention is directed to a system including a machine-readable memory, such as a computer and/or a calculator, and a processor configured to compute said mathematical function, in particular said multivariate Cox function. This system may be dedicated to perform the method according to the invention.

Another object of the present invention is a kit for implementing the method of the present invention, wherein the kit comprises reagents for measuring radiomimetic agent-induced T cell apoptosis, as defined in the present invention.

Another object of the present invention is a kit for implementing the method of the present invention, wherein the kit comprises:
- a box/container and bag suited for biological transportation of a T cell containing sample, in particular a blood sample, and optionally reagents for isolating T cells; and
- reagents for measuring radiomimetic agent-induced T cell apoptosis.

Another object of the present invention is thus a kit for detecting the risk of developing a ionizing radiation-induced side effect in a subject using the method of the present invention, wherein said kit comprises:
- a box/container and bag suited for biological transportation of a T cell containing sample, in particular a blood sample, and optionally reagents for isolating T cells
- reagents for determining radiomimetic agent-induced T lymphocyte apoptosis as defined in the present invention.

By "kit" is intended any manufacture (e.g., a package or a container). The kit may be promoted, distributed, or sold as a unit for performing the methods of the present invention. Furthermore, any or all of the kit reagents may be provided within containers that protect them from the external environment, such as in sealed containers. The kits may also contain an instructional material describing the kit and methods for its use. Kits are also provided that are useful for various purposes. The label or instructional material may provide a description of the content of the kit as well as instructions for the intended use.

In one embodiment, the reagents for determining radiomimetic agent-induced T lymphocyte apoptosis as defined in the present invention correspond to some or all specific reagents required to:
- run the step of culture of T cells as described hereinabove, in the presence of at least one radiomimetic agent, such as, for example, a culture medium suitable for culturing T cells (such as, for example, RPMI supplemented with 20% FCS), and said radiomimetic agent (such as, for example, bleomycin);
- run the apoptosis measurement assay (for example, using a flow cytometer), such as, for example, propidium iodide, fluorochrome coupled-annexin, YO-PRO dyes, PO-PRO dyes, Resazurin, Hoechst, fluorochrome coupled-caspases.

In one embodiment, the in vitro method of the invention is a method for assessing the individual radiosensitivity of a subject with a breast cancer (preferably for determining the risk of developing ionizing radiation-induced breast late side effects), and the method of the invention comprises:

a) contacting a T cell containing sample previously obtained from a subject, with at least one radiomimetic agent;
b) measuring a radiomimetic agent-induced T lymphocyte apoptosis in the sample;
c) determining the level of at least two clinical parameters in the subject,
d) optionally measuring at least one biochemical marker in the subject, and
e) optionally combining in a mathematical function, the radiomimetic agent-induced T cell apoptosis measured in step b) with said at least two clinical parameters determined at step c), and optionally with the at least one biochemical marker measured at step d).

By "clinical parameter" it is meant any clinical parameter related to the subject and relevant to assess an increased risk of ionizing treatment-induced toxicity in said subject. Examples of clinical parameters include, but are not limited to, age, breast volume, adjuvant hormonotherapy, boost (complement dose of irradiation), node irradiation, and tobacco smoking. Preferably, the at least two clinical parameters measured at step c) comprise tobacco smoking habits and adjuvant hormonotherapy. In one embodiment, the method of the invention comprises determining in step (c) if the subject previously received or is currently receiving an adjuvant hormonotherapy. As used herein, the term "adjuvant hormonotherapy" refers to a treatment started after or concomitantly or before surgery, chemotherapy, and/or ionizing radiation therapy to lower the risk of recurrence of the cancer.

Hormone receptor-positive breast cancer depends on hormones called estrogen and/or progesterone to grow. Adjuvant hormonotherapy allows to lower the levels of these hormones in the body or to block the hormones from getting to any remaining cancer cells.

Examples of adjuvant hormonotherapy that may be used for the treatment of breast cancer include, but are not limited to, tamoxifen, aromatase inhibitors (AIs), such as anastrozole (Arimidex) and letrozole (Femara), exemestane (Aromasin), and ovarian suppression by surgery or by drugs selected from gonadotropin, luteinizing, goserelin (Zoladex) and leuprolide (Lupron).

In one embodiment, the method of the invention comprises determining in step (c) the tobacco smoking habits of the subject.

As used herein, the terms "determining the tobacco smoking habits of the subject" means determining if the subject is a tobacco smoking subject (either daily smoker, intermittent smoker or non-daily smoker) or a non-smoking subject as defined hereafter.

A "daily smoker" may be defined as a subject that is currently smoking on a daily basis. A "intermittent smoker" may be defined as a subject not smoking on a daily basis (DiFranza et al., 2007; Lindstrom, Isacsson, & the Malmo Shoulder-Neck Study Group, 2002) or smoking on 1-15 days in the previous month (McCarthy, Zhou, & Hser, 2001). A "non-daily smoker" may be defined as a subject (i) smoking at least weekly (but not daily) or less often than weekly; (ii) smoking at least 100 cigarettes in the lifetime and currently smoking some days; (iii) smoking more than 100 cigarettes in the lifetime, currently smoking some days, and having smoked less than 30 cigarettes during the past 30 days; (iv) smoking more than 100 cigarettes in the lifetime and having smoked some days or 1-2 days in the previous 30 days; or (v) smoking fewer than 100 cigarettes in the lifetime and having smoked in the previous 30 days (Gilpin, White, & Pierce, 2005; Hassmiller et al., 2003; Husten, McCarty, Giovino, Chrismon, & Zhu, 1998; Leatherdale, Ahmed, Lovato, Manske, & Jolin, 2007; McDermott et al., 2007; Tong, Ong, Vittinghoff, & Perez-Stable, 2006; Wortley, Husten, Trosclair, Chrismon, & Pederson, 2003).

A "some-day smoker" may be defined as a subject having ever smoked 100 cigarettes during the smoker's lifetime and currently smoking on some days (not every day; CDC, 1993; Hassmiller, Warner, Mendez, Levy, & Romano, 2003).

A "never daily smoker" may be defined as a subject having never smoked daily for 6 months or more (Gilpin et al., 1997).

In one embodiment, the method of the invention comprises measuring at step d) at least one biochemical marker. In one embodiment, said at least one biochemical marker is selected from the group comprising proteins of individual radiosensitivity and genes of individual radiosensitivity.

In one embodiment, said at least one biochemical marker is a protein of individual radiosensitivity, preferably selected from the group consisting of AK2 (adenylate kinase 2), HSPA8 (Heat shock cognate protein 71 kDa, also referred to as HSC70), ANX1 (Annexin 1), APEX1 (DNA-(apurinic or apyrimidinic site) lyase) and IDH2 (mitochondrial isocitrate dehydrogenase 2), fragments and combinations thereof.

In one embodiment, said at least one biochemical marker is a combination of at least two proteins of individual radiosensitivity, of at least three proteins of individual radiosensitivity, of at least four proteins of individual radiosensitivity, or of five proteins of individual radiosensitivity, preferably selected from the group consisting of AK2, HSPA8, ANX1, APEX1 and IDH2.

As used herein, a "protein of individual radiosensitivity" refers to a protein whose expression (either at the protein or RNA level) is indicative of the individual radiosensitivity of the subject.

Consequently, in one embodiment, measuring at least one biochemical marker at step (c) corresponds to measuring a protein level of at least one protein of individual radiosensitivity in a sample from the subject or to measuring a nucleic acid encoding said protein in a sample from the subject. In one embodiment, in a first step, proteins and/or nucleic acids are isolated from a biological sample previously obtained from the subject. A method according to the invention may thus include protein or nucleic acid extraction, purification and characterization, using well known biochemistry methods. The presence or level of said protein of individual radiosensitivity may be determined by methods well known in the art. Examples of such methods include, but are not limited to, a method based on immune-detection, a method based on western blot, a method based on mass spectrometry, a method based on chromatography, or a method based on flow cytometry, and a method for specific nucleic acid detection. Specific examples of in vitro methods for determining a protein level in a sample are well-known in the art, and include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In one embodiment, the presence and level of expression of proteins can be determined directly or be analyzed at the nucleic level by detecting, and preferably quantifying, protein-specific nucleic acids, and particularly mRNA (i.e., assessing the transcription level of the protein). Methods for assessing the transcription level of a protein are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

In one embodiment, said at least one biochemical marker is a gene of individual radiosensitivity, preferably selected from the group consisting of TGFβ, SOD2, TNFα, and XRCC1.

As used herein, a "gene of individual radiosensitivity" refers to a gene whose expression (either at the protein or RNA level) is indicative of the individual radiosensitivity of the subject, or to a gene comprising at least one single nucleotide polymorphism (SNP) indicative of the individual radiosensitivity of the subject, or involved in the fibrosis pathway and ROS management.

Consequently, in one embodiment, measuring at least one biochemical marker at step (c) corresponds to measuring an expression level of or determining the presence of a SNP in at least one gene of individual radiosensitivity in a sample from the subject.

The presence or level of expression of said gene of individual radiosensitivity may be determined by a usual method known from man skilled in the art. A non-limiting list of such methods is shown hereinabove.

In one embodiment, the in vitro method for determining presence or level of expression of a gene of individual radiosensitivity is as disclosed in Azria et al., 2008 and includes lymphocyte isolation, DNA extraction and amplification, and denaturating high-performance liquid chromatography or the Surveyor nuclease assay using a Transgenomic WAVE High Sensitivity Nuclei Acid Fragment Analysis System.

In one embodiment, the in vitro method of the invention comprises measuring at step (c) at least one protein of individual radiosensitivity and at least one gene of individual radiosensitivity.

In one embodiment, the in vitro method of the invention comprises:
a) contacting a T cell containing sample previously obtained from a subject, with at least one radiomimetic agent;
b) measuring a radiomimetic agent-induced T lymphocyte apoptosis in the sample;
c) determining if the subject is/was treated with an adjuvant hormonotherapy, and determining the tobacco smoking habits of the subject,
d) optionally measuring at least one biochemical marker in the subject, and
e) optionally combining in a mathematical function, the radiomimetic agent-induced T cell apoptosis measured in step b) with said at least two clinical parameters determined at step c), and optionally with the at least one biochemical marker measured at step d).

In one embodiment, the method of the invention comprises at step e) a step of combining the radiomimetic agent-induced T cell apoptosis measured in step (b), the at least two clinical parameters measured at step c) (preferably presence or absence of an adjuvant hormonotherapy, and tobacco smoking habits) and optionally the at least one biochemical parameter measured in step d) in a mathematical function, thereby obtaining an end-value.

In one embodiment, said mathematical function is a multivariate analysis using a binary logistic regression, a multiple linear regression or any time-dependent regression.

In one embodiment, said mathematical function is a Cox proportional hazard regression model.

In one embodiment, for the clinical parameters as listed hereinabove and that may be present or absent, the presence of said parameter is given value=1 in the mathematical function, preferably in the multivariate Cox function, while its absence is given value=0 in the mathematical function, preferably in the multivariate Cox function.

For example, in one embodiment, at step (c), if the subject is treated by an adjuvant hormonotherapy, the value "1" is affected. In one embodiment, at step (c), if the subject is not treated by an adjuvant hormonotherapy, the value "0" is affected to the subject.

In one embodiment, for the clinical parameter "tobacco smoking", a tobacco smoking patient is defined consistently as daily smoker, intermittent smoker or non-daily smoker (and given value=1 in the mathematical function, preferably in the multivariate Cox function), while a non-smoking patient is defined as some-day smoker or never daily smoker (and given value=0 in the mathematical function, preferably in the multivariate Cox function).

In one embodiment, for the clinical parameter "age", the median age is 55 years to define patients being 55 years old or less (and given value=0 in the mathematical function, preferably in the multivariate Cox function) and patients being older than 55 years old (and given value=1 in the mathematical function, preferably in the multivariate Cox function).

In another embodiment, for continued data (in particular for the biochemical markers optionally measured at step d) and for the radiomimetic agent-induced T cell apoptosis measured at step b)), the parameter is given its exact value in the mathematical function, preferably in the multivariate Cox function.

In one embodiment, the mathematical function of the invention is a binary logistic regression, a multiple linear regression or any time-dependent regression.

In one embodiment, the end-value is obtained by combining the measures of radiomimetic agent-induced T lymphocyte apoptosis, at least two clinical parameters (preferably adjuvant hormonotherapy and tobacco smoking habits), and optionally at least one biochemical marked, in a regression formula established using multivariate analysis.

In one embodiment, said formula is expressed as:

A+B1*(radiomimetic agent-induced T lymphocyte apoptosis)+B2*(first clinical parameter, preferably adjuvant hormonotherapy)+B3*(second clinical parameter, preferably tobacco smoking habits)+ . . . +Bn*((n−1) clinical parameter or biochemical marker), wherein A, B1, B2, . . . , Bn are predetermined coefficients.

In another embodiment, said formula is expressed as:

C+[D1*LN(radiomimetic agent-induced T lymphocyte apoptosis)]+[D2*LN(first clinical parameter, preferably adjuvant hormonotherapy)]+[D3*LN(second clinical parameter, preferably tobacco smoking habits)]+ . . . + [Dn*LN((n−1) clinical parameter or biochemical marker)], wherein C, D1, D2, . . . Dn are predetermined coefficients.

In another embodiment, said formula is expressed as:

E+exp[F1*(radiomimetic agent-induced T lymphocyte apoptosis)]+[F2*(first clinical parameter, preferably adjuvant hormonotherapy)]+[F3*(second clinical parameter, preferably tobacco smoking habits)]+ . . . +[Fn*((n−1) clinical parameter, or biochemical marker)], wherein E, F1, F2, . . . , Fn are predetermined coefficients.

In one embodiment, the regression is a multivariate Cox regression.

In one embodiment, said regression is time-dependent, preferably is a time-dependent multivariate regression.

In one embodiment, said regression is a multivariate time-related model, preferably a Cox proportional hazard regression model.

In one embodiment of the present invention, the independent parameters combined in the Cox regression are radiomimetic agent-induced T lymphocyte apoptosis, adjuvant hormonotherapy, tobacco smoking habits and optionally at least one biochemical markers. In one embodiment of the present invention, the independent parameters combined in the Cox regression are radiomimetic agent-induced T lymphocyte apoptosis, adjuvant hormonotherapy, and tobacco smoking habits.

The multivariate Cox function may usually be obtained by combining the relative weight of each parameter, as individually determined in the multivariate Cox regression, with a negative sign when the markers harbor a negative correlation with the observation of breast late side effect.

In one embodiment, in order to define the multivariate Cox model of the invention (i.e., "modelling"), a classification of breast cancer patients is made based on the detection of ionizing radiation-induced side effects, preferably of breast late side effects as described hereinabove, during the clinical follow-up of studies.

In one embodiment, said modelling may be based on a population (e.g., a multicenter population) of breast cancer patients treated by ionizing radiation (which may be named "reference population"). The steps to build up the model may thus consist in:

the measurement of the percentage of radiomimetic agent-induced T lymphocyte apoptosis in all the subjects of the population;

the identification of biochemical markers (e.g, proteins and/or genes of individual radiosenstivity) and of clinical parameters relevant to assess an increased risk of ionizing radiation toxicity in a subject;

the use of said identified biochemical markers and clinical parameters in a multicenter clinical trial to identify relevant variables as prognostic factors of ionizing radiation-induced side effects, in particular breast late side effects, i.e., as variables that are indicative of a specific risk to develop ionizing radiation-induced side effects, in particular breast late side effects;

the application of these variables on the large multicenter clinical trial to identify the predictive role of the combination of the radiomimetic agent-induced T lymphocyte apoptosis, biochemical markers (e.g, proteins and/or genes of individual radiosensitivity) and of clinical parameters for developing ionizing radiation-induced side effects, in particular breast late side effects.

By "multicenter research trial" it is meant a clinical trial conducted at more than one medical center or clinic.

In one embodiment, the multivariate Cox model is:

Hazard (experiencing a ionizing radiation-induced side effect)=baseline hazard*exp(($\beta 1$*radiomimetic agent-induced T lymphocyte apoptosis)+$\beta 2$*(first clinical parameter, preferably adjuvant hormonotherapy)+$\beta 3$*(second clinical parameter, preferably tobacco smoking habits)+ . . . $\beta n$* (Clinical parameter (n−1) or biochemical marker with n superior or equal to 3), where the baseline hazard corresponds to the hazard of experiencing the event (ionizing radiation-induced side effect) when all covariates are zero.

In another embodiment, the multivariate Cox model is:

Hazard (experiencing a ionizing radiation-induced side effect)=baseline hazard*exp(($\beta 1$*radiomimetic agent-induced T lymphocyte apoptosis)+β2*(adjuvant hormonotherapy)+β3*(tobacco smoking habits), where the baseline hazard corresponds to the hazard of experiencing the event (ionizing radiation-induced side effect) when all covariates are zero.

The right-hand side of the above equation specify the underlying function of the model. The left-hand side of the equation is the predicted probability that may be presented in a nomogram and communicated to the breast cancer patient. Beta coefficients must be estimated for each covariate and converted to hazard ratios as a measure of effect, as in any statistical report. To obtain the predicted probability of the event in question (experiencing a ionizing radiation-induced side effect), the above equation is calculated using a patient's individual characteristics and the model-derived beta coefficients.

In one embodiment, the baseline hazard is a constant corresponding to the basal risk to develop a ionizing radiation-induced side effect, without any co-variables. During modelling according to Cox regression model, this baseline hazard may be determined from data coming from a reference population as disclosed above.

Clinical parameters '1' to 'n' may be selected in the list of clinical parameters or disease parameters or ionizing radiation treatment parameters as disclosed hereinabove. In one embodiment, said clinical parameters are selected from the list comprising age, breast volume, adjuvant hormonotherapy, boost (complement dose of irradiation), node irradiation, and tobacco smoking. In one embodiment, said clinical parameters include adjuvant hormonotherapy and tobacco smoking habits.

In one embodiment, Hazard (experiencing a ionizing radiation-induced side effect)=baseline hazard*exp((β1*radiomimetic agent-induced T lymphocyte apoptosis)+β2*(first clinical parameter, preferably adjuvant hormonotherapy)+β3*(second clinical parameter, preferably tobacco smoking habits)+ . . . βn*(Clinical parameter (n−1) or biochemical marker with n superior or equal to 3), where the baseline hazard corresponds to the hazard of experiencing the event (ionizing radiation induced side effects, preferably breast late side effect) when all covariates are zero.

In one embodiment, the value entered for a given parameter in the formula hereinabove is 0 if said parameter is absent and 1 if said parameter is present (such as, for example, for the presence or absence of an adjuvant hormonotherapy).

In another embodiment, the value entered for a given parameter in the formula hereinabove corresponds to the measured value of said parameter (such as, for example, for the radiomimetic agent-induced T lymphocyte apoptosis).

In one embodiment, Hazard (experiencing a ionizing radiation-induced side effect)=baseline hazard*exp (β1*radiomimetic agent-induced T lymphocyte apoptosis)+β2*(adjuvant hormonotherapy [0=no; 1=yes])+, β3*(tobacco smoking [0=no; 1=yes]) where the baseline hazard corresponds to the hazard of experiencing the event (ionizing radiation induced side effects, preferably breast late side effect) when all covariates are zero.

In one embodiment, Hazard (experiencing a ionizing radiation-induced side effect) may also be named risk to develop a ionizing radiation-induced side effect, for a breast cancer subject.

In one embodiment, based on this multivariate Cox function, the skilled person would be able to introduce any additional relevant biochemical marker(s) and/or clinical parameter(s) to said multivariate Cox model.

In one embodiment, the different coefficients used for the values obtained for the different markers in the function of the invention, preferably in the multivariate Cox regression can be calculated through statistical analysis in a reference population of patients.

In one embodiment, the method of the invention thus comprises measuring an end-value, wherein said end-value is indicative of the risk of the subject to develop a ionizing radiation-induced side effect as described hereinabove. In one embodiment, said risk is estimated taken into account a basal risk (baseline characteristics) and co-variables (biochemical markers and clinical parameters, which are combined in a mathematical function).

Therefore, in one embodiment, the "end-value" is the predicted probability of occurrence of a ionizing radiation-induced side effect for each subject.

In one embodiment, depending on the end-value obtained for a subject, it is possible to predict for said subject the risk of developing a ionizing radiation-induced side effect, during follow-up after ionizing radiation treatment, such as, for example, 3 months or 6, 12, 18, 24, 30 or 36 months after the end of the ionizing radiation treatment. For example, in one embodiment, an end-value of 92% means an 8% risk to developing a ionizing radiation-induced side effect, during ionizing radiation and/or during the follow-up after ionizing radiation, such as, for example, 1 month, 3, 6, 12, 18, 24, 30 or 36 months after the end of the ionizing radiation.

In one embodiment, the method of the invention comprises comparing the end-value obtained for a subject with a reference end-value.

In one embodiment, the reference end-value corresponds to the end-value measured in a reference population of breast cancer patients. In one embodiment, the reference end-value was measured in a reference population comprising breast cancer patients, treated with ionizing radiation and having experienced ionizing radiation-induced side-effects during follow-up (such as, for example, during ionizing radiation and/or during the follow-up after ionizing radiation, such as, for example, 1 month, 3, 6, 12, 18, 24, 30 or 36 months after the end of the ionizing radiation). In another embodiment, the reference end-value was measured in a reference population comprising breast cancer patients, treated with ionizing radiation and having experienced no ionizing radiation-induced side-effects during follow-up (such as, for example, during ionizing radiation and/or during the follow-up after ionizing radiation, such as, for example, 1 month, 3, 6, 12, 18, 24, 30 or 36 months after the end of the ionizing radiation).

A reference end-value can be derived from population studies, including without limitation, such subjects having similar age range, subjects in the same or similar ethnic group, similar breast cancer history, similar ionizing radiation treatment and the like.

In one embodiment, the reference value is constructed using algorithms and other methods of statistical and structural classification.

In one embodiment, the reference end-value corresponds to the mean end-value measured in the reference population. In one embodiment of the invention, the reference end-value corresponds to the median end-value measured in the reference population.

In one embodiment, the method of the invention is computerized (or computer-implemented).

In one embodiment, the method of the invention comprises determining if the end-value is superior to the reference end-value, or inferior or equal to said reference end-value.

In another embodiment, the method of the invention comprises determining the percentile wherein the end-value measured for the subject may be positioned. According to this embodiment, the end-values measured in a reference population are classified in percentiles, wherein the end-values obtained for all subjects of the reference population are ranged according to their numerical value in ascending order. In one embodiment of the invention, the percentiles are percentiles of subjects, i.e., each percentile comprises the same number of subjects. Therefore, the first percentile corresponds to subjects with the lowest end-values, while the last percentile corresponds to subjects with the highest end-values. In one embodiment, when three percentiles are drawn, each percentile is named a tertile. In another embodiment, when four percentiles are drawn, each percentile is named a quartile. In another embodiment, when five percentiles are drawn, each percentile is named a quintile.

The skilled artisan knows how to determine the reference end-values from radiomimetic agent-induced T cell apoptosis values obtained in a reference population. A non-limiting example of such method include the drawing of a ROC curve to determine the cut-off of end-value measured for the subject with side effect vs subject without side effect (AU-ROC) which maximize Se and Sp.

In one embodiment, determining the end-value for a breast cancer patient, will help the physician to adapt the dose and sequences of ionizing radiation treatment to the patient to limit the breast late side effects, and optionally to adapt the treatment by replacing ionizing radiation treatment with other therapeutic treatments.

In a particular embodiment, the end-value (for example obtained with a multivariate Cox function) is used to choose a suitable treatment for the patient, such as an appropriate ionizing radiation regimen, or to choose between a mastectomy or conserving surgery.

The volume of irradiation and the prescription dose may thus be discussed according to the level of risk. In one embodiment, if the end-value is superior to a reference value, there is a risk of developing a ionizing radiation side effect (preferably a breast late side effect) after ionizing radiation treatment. In one embodiment, the reference value ranges from about 85 to about 95, such as, for example, is of about 85, 86, 87, 88, 89, 90, 91, 92, 93, 94, or 95. Absence of boost ionizing radiation therapy, absence of node irradiation and dose per fraction less than 2.5 Gy will be different treatment possibilities in case of high risk of ionizing radiation side effect (preferably a breast late side effect) and low risk of recurrences of optimal clinical benefit.

In one embodiment, the end value is used to choose a suitable treatment for the breast cancer patient, such as an appropriate ionizing radiation therapy dosage regimen, wherein:
  if the patient presents a risk to develop breast late side effect, the appropriate ionizing radiation dosage regimen will be decreased (such as, for example by delivery of partial breast hypofractionated treatment);
  if the patient presents low risk or no risk to develop breast late side effect, the appropriate ionizing radiation dosage regimen may be increased (such as, for example by delivery of hypofractionated treatment (e.g., 5 or 16 fractions, which are the common numbers of fractions in such treatments)).

In one embodiment, a patient with a risk to develop a breast late side effect ranging from about 5 to about 15% (i.e., with an end-value ranging from about 85 to about 95%), such as, for example, a patient with a risk of about 5, 6, 7, 8, 9, 10, 11, 12, 13, 14 or 15% (i.e., with an end-value of respectively about 95, 94, 93, 92, 91, 90, 89, 88, 87, 86 or 85%), the breast cancer patient is considered to be a (high) risk patient.

In one embodiment, a patient with a risk to develop a breast late side effect is less than about 5% (i.e., with an end-value superior to about 95%), such as, for example, a patient with a risk of about 1, 2, 3, 4, or 5% (i.e., with an end-value superior, respectively, to about 99, 98, 97, 96 or 95%), the breast cancer patient is considered to be a low risk patient.

In another embodiment, the end value is used in the decision of performing an immediate breast reconstruction after conserving surgery or mastectomy. In one embodiment, if said end value ranges from about 85 to about 95%, such as, for example, of about 95, 94, 93, 92, 91, 90, 89, 88, 87, 86 or 85%, an immediate breast reconstruction after conserving surgery or mastectomy would be considered.

Another object of the invention is a method for implementing an adapted patient care for a breast cancer patient, wherein said method comprises:
  assessing the risk for said patient to develop ionizing radiation-induced side-effects, using the in vitro method as described hereinabove;
  implementing an adapted patient care depending on the risk for the patient to develop ionizing radiation-induced side-effects.

In one embodiment, the patient is a high risk patient and the adapted patient care may be selected from the group comprising decreased ionizing radiation dosage regimen, mastectomy, absence of boost ionizing radiation therapy, absence of node irradiation and dose per fraction less than 2.5 Gy.

In one embodiment, the patient is a low risk patient and the adapted patient care may be selected from the group comprising increased ionizing radiation dosage regimen (such as, for example by delivery of hypofractionated treatment), and immediate breast reconstruction after conserving surgery or mastectomy.

Another object of the present invention is thus a computer software for implementing the method of the invention.

In one embodiment, the in vitro method of the invention is implemented with a microprocessor comprising a software configured to calculate an end-value resulting from the combination of the measures of radiomimetic agent-induced T lymphocyte apoptosis and at least two clinical parameters (preferably adjuvant hormonotherapy and tobacco smoking habits), and optionally at least one biochemical marker.

In one embodiment, the in vitro method of the invention is implemented with a microprocessor comprising a software configured to calculate an end-value resulting from the combination of the measures of radiomimetic agent-induced T lymphocyte apoptosis and at least two clinical parameters (preferably adjuvant hormonotherapy and tobacco smoking habits), and optionally at least one biochemical marker.

Another object of the present invention is directed to a system including a machine-readable memory, such as a computer and/or a calculator, and a processor configured to compute said mathematical function, in particular said multivariate Cox function. This system may be dedicated to perform the method according to the invention.

In particular embodiment, said system comprises additionally a module for executing a software to build a nomogram (linear predictor between 0-100 for each parameter including main effect, interaction and piecewise linear effect) and calculate the risk (corresponding to the end-value) for the subject to develop a ionizing radiation-induced side-effect.

In one embodiment, the in vitro method of the invention thus comprises:
- contacting T cells with at least radiomimetic agent for all subjects of a reference population and measuring radiomimetic agent-induced T cells apoptosis
- optionally measuring at least one biochemical marker for all subjects of the reference population
- measuring at least two clinical parameters, preferably adjuvant hormonotherapy and tobacco smoking, for all subjects of the reference population;
- univariate analysis (estimation for each parameter one by one in order to select all significant parameters with p-value≤0.2) under a Cox regression model;
- multivariate analysis (estimation including all selected parameters by univariate analysis+adding optional non-significant parameters which are clinically relevant) under Cox regression model;
- selection of significant parameters and/or clinically relevant parameters to obtain the final model whose linear predictor were extracted to estimate the risk (probability) to develop a ionizing radiation-induced side effect; linear predictor was integrated in a software;
- execution of a software to build a nomogram according to Iasonos et al. 2008 (linear predictor between 0-100 for each parameter including main effect, interaction and piecewise linear effect). This representation thus gives the risk (probability) of developing a ionizing radiation-induced side effect by calculation of an end-value after ionizing radiation for each breast cancer patient according to each individual parameter.

Therefore, in one embodiment, the present invention comprises visualizing the end-value obtained for the breast cancer subject on a nomogram. A nomogram is a popular visual plot to display the predict probabilities of occurrence of an event for decision support.

In one embodiment, to build this nomogram after fitting the Cox multivariate model, a linear predictor is obtained according to the method described by Iasonos et al. (2008). Another object of the present invention is thus a user-friendly interface, i.e., a nomogram, computer or calculator, implementing said mathematical combination (preferably said multivariate Cox function), to help physician to interpret the risk of developing a ionizing radiation-induced side effect, e.g., a breast late side effect during and/or after a ionizing radiation treatment. Accordingly, the present invention encompasses a nomogram implementing the mathematical function of the invention (preferably the multivariate Cox function according to the invention).

As used herein, "a nomogram" refers to a graphical representation of prognosis formula(ae) from a mathematical function as described herein, such as, for example, a multivariate Cox modelling, which allows for estimation of the risk of developing a ionizing radiation-induced side effect, in a subject. In one embodiment, said nomogram is based on one or more readily obtained parameters, including, but not limited to, radiomimetic agent-induced T cell apoptosis, adjuvant hormonotherapy, and tobacco smoking.

The usefulness of a nomogram is that it maps the predicted probabilities into points on a scale from 0 to 100 in a user-friendly graphical interface. The total points accumulated by the various covariates correspond to the predicted risk for a patient.

According to one embodiment, the method of the invention comprises implementing the data obtained at step b), at step c) and optionally at step d) to a computer or a calculator that will calculate the mathematical combination (preferably the multivariate Cox regression) and the risk of developing of a ionizing radiation-induced side effect. The data obtained by the physician is therefore more easily interpretable, and will allow for an improvement in the process for deciding the adapted patient care.

Another object of the present invention is a kit for implementing the method of the invention, in particular for collecting data of a subject to be further used for detecting the risk of developing of a ionizing radiation-induced side effect in a breast cancer subject using the method of the present invention, wherein the kit comprises:
- a box/container and bag suited for biological transportation of a T cell containing sample, in particular a blood sample, and optionally reagents for isolating T cells;
- reagents for measuring radiomimetic agent-induced T cell apoptosis, and optionally at least one biochemical marker as defined herein; and
- forms to be completed by the patient and/or the nurse and/or the physician, specifically designed and necessary to implement the method of the invention.

As an example, the forms may contain specific questions aimed at collecting information necessary to run the predictive analysis such as, age, whether the patient has undergone or will undergo an adjuvant treatment (chemotherapy or hormone therapy, for example), tobacco habit and date and time when the T cell containing sample was recovered.

Another object of the present invention is thus a kit for detecting the risk of developing a ionizing radiation-induced side effect (preferably a breast late side effect), in a subject using the method of the present invention, wherein said kit comprises:
- reagents for determining radiomimetic agent-induced T lymphocyte apoptosis as defined in the present invention;
- optionally means for collecting information on the at least two clinical parameters (preferably adjuvant hormonotherapy and tobacco smoking habits) according to the present invention, such as a survey;
- optionally means for measuring at least one biochemical marker according to the present invention; and
- optionally a nomogram according to the invention.

In one embodiment, the reagents for determining radiomimetic agent-induced T lymphocyte apoptosis as defined in the present invention correspond to some or all specific reagents required to:
- run the step of culture of T cells as described hereinabove, in the presence of at least one radiomimetic agent, such as, for example, a culture medium suitable for culturing T cells, and said radiomimetic agent (such as, for example, bleomycin);
- run the apoptosis measurement assay (for example, using a flow cytometer), such as, for example, propidium iodide, fluorochrome coupled-annexin, YO-PRO dyes, PO-PRO dyes, Resazurin, Hoechst, fluorochrome coupled-caspases.

In one embodiment, the reagents for determining the values of at least one biochemical marker according to the invention correspond to some or all specific reagents required to run the proteins and/or genes biosensitivity measurement assay in an independent laboratory.

In one embodiment, the means for collecting information of at least two clinical parameters according to the invention correspond to specific forms to be completed by the patient and/or the nurse and/or the physician, specifically designed and required to run the method of the invention and the nomogram analysis. In a preferred embodiment, these forms may contain specific questions aimed at collecting information necessary to run the predictive analysis such as whether the patient has undergone or will undergo an adjuvant treatment (chemotherapy, hormonotherapy, for example), and tobacco habit.

Examples

The present invention is further illustrated by the following examples.

Materials and Methods

Blood Sample

Blood samples were purchased from Etablissement Français du Sang (EFS) with the convention number 21PLER2016-0100 AV01. Blood samples were collected from healthy donors in 5 mL heparinized tubes without separation gel.

Culture Conditions

Blood cells were grown in RPMI-1640 with glutamax (Fisher scientific, France) supplemented with 20% fetal calf serum (FCS) (EuroBio, France). Cells were maintained at 37° C. with 5% $CO_2$ during the experiments.

Products

Bleomycin (EuroMedex) was solubilized in sterile MilliQ water at 50 mg/mL according to manufacturer instructions and stored at −80° C.

Radiation-Induced CD8 T-Lymphocyte Apoptosis (RILA) Procedure

The protocol was adapted from studies of Ozsahin et al. (Ozsahin, Crompton et al. 2005).

Before radiotherapy (RT), one blood sample was collected from each patient in a 5-mL heparinized tube. Twenty or twenty-four hours after blood collection, 200 μl of blood were aliquoted into a 6-well plate containing 2 mL of RPMI-20% FCS. All tests were carried out in triplicate for both 0 and 8 Gy. Ex-vivo irradiations were delivered after 24 hours of blood cell culture using the Xenx irradiator platform (XStrahl, UK). Then, the plates were immediately incubated for 48 hours at 37° C. (5% $CO_2$).

Samples were then centrifuged for 5 min at 300 g. The pellets were resuspended in phosphate-buffered saline (PBS) containing 10 μl of anti-human CD8-FITC antibody (Becton Dickinson, USA) and incubated for 20 minutes at room temperature. Then, red blood cells were lysed by addition of 4 ml of lysis buffer diluted 1:10 in water (Becton Dickinson, USA). After another 20 minutes incubation time at room temperature, samples were centrifuged for 5 min at 300 g and the pellets were washed with 3 ml of PBS. Pellets were suspended in 200 μl of PBS containing 25 μg/ml of propidium iodide (Sigma, France) and 5 μl of RNAse A at 10 mg/ml (Qiagen, France). The samples were analyzed by flow cytometry within the next hours, using the CytoFlex (Beckman Coulter, USA).

Bleomycin-Induced CD8 T-Lymphocyte Apoptosis Procedure

Irradiation and Treatment on Blood Samples

Different irradiation doses (0 Gy, 6 Gy, 8 Gy and 10 Gy) and different Bleomycin concentrations (50 μg/mL, 100 μg/mL, 150 μg/mL, 200 μg/mL, 250 μg/mL) were applied to aliquots of the same blood sample.

Irradiations and culture were performed as previously described. The staining was performed 48 hours after the irradiation using the same protocol as previously described.

For the Bleomycin treatment, 2 protocols were tested:

Treatment 24 hours after blood cell culture

Two hundred microliters of blood were aliquoted into a 6-well plate containing 2 mL of RPMI-20% FCS, about 24 hours after blood collection. Bleomycin treatment, at the different concentrations, was performed 24 hours after blood cell culture by adding the Bleomycin directly into the wells. The staining for detecting apoptosis was performed as described above and 48 hours after the bleomycin treatment (thus, after less than 50 hours of contact of bleomycin with the cells).

Treatment during blood cell culture:

Two hundred microliters of blood were aliquoted into a 6-well plate containing 2 mL of RPMI-20% FCS-bleomycin, about 24 hours after blood collection. The cell culture media containing the different concentrations of bleomycin were made fresh just before starting the cell culture. After bleomycin incubation with blood cells for at least 50 hours (generally more than about 60 hours, in particular between 65 and 75 hours), samples were stained for flow cytometry analysis as described above.

Statistical Analysis

Two mixed linear models with fixed intercept, fixed slope and random intercept were used to model the RILA rate evolution according to the compound or to the irradiation dose in Gray.

Analysis were performed with the R software (version 3.3.1)

Results

Prolonged Bleomycin Treatment Induces a Similar T Lymphocyte Apoptosis Rate than an 8 Gy Irradiation The aim of this study is to determine the bleomycin conditions of use to obtain a similar T lymphocyte apoptosis rate than an 8 Gy irradiation.

Two treatment conditions were tested on the same blood sample: blood cells were treated by several bleomycin concentrations 24 hours after cell culture or from the start of cell culture. A control experiment was performed by irradiating blood samples at 8 Gy.

The results described in the Table 1 are representative of all experiments. Blood samples were treated by a concentration of bleomycin between 50 μg/mL and 500 μg/mL. When the treatment was performed 24 hours after blood cell culture, no bleomycin concentration, applied for less than 50 hours, induces the apoptosis rate observed after 8 Gy irradiation.

In contrast, when treatment was applied at the start of blood cell culture, the apoptosis rate obtained after irradiation was achieved with a bleomycin concentration lower than 300 μg/ml. These results show that the treatment must be performed during at least 50 hours (such as, for example, with a treatment starting with the cell culture) to obtain a similar T lymphocyte apoptosis rate than an 8 Gy irradiation. Without willing to be bound to any theory, it is suggested that bleomycin may need more time to induce the same T lymphocyte apoptosis rate as an 8 Gy irradiation. It is to be noted that the duration of contact of the bleomycin with the cells may vary according to the concentration of the bleomycin, but should be long enough (i.e. more than 50 hours) in order to be able to reproduce the apoptosis level observed in RILA.

However, it is preferred to use low concentrations of bleomycin, as it is an expensive compound.

TABLE 1

Comparison of bleomycin treatment on the same blood sample applied during cell culture or 24 hours later.

| 8 Gy irradiation (%) | T lymphocytes apoptosis rate (%) 28.2 | |
|---|---|---|
| Bleomycin treatment | From the start of cell culture (%) | 24 hours after cell culture (%) |
| 50 µg/mL | 12.47 | 3.98 |
| 100 µg/ml | 19.14 | 2.72 |
| 200 µg/ml | 23.44 | 10.13 |
| 300 µg/ml | 26.32 | 11.9 |
| 400 µg/ml | 30.68 | 16.78 |

This table clearly shows that the exposition of the bleomycin to the cells from the start of cell cultures (thereby prolonging the exposition of the cells to the compound) leads to a higher level of apoptosis of the T lymphocytes cells than when bleomycin is added from 24 hours after start culture. One can see that the prolongation of exposure leads to a great increase of apoptosis, whatever the concentration of bleomycin.

Identification of a Correlation Between Bleomycin Treatment and Irradiation

In order to characterize the correlation between bleomycin treatment and irradiation, different bleomycin concentrations and different irradiation doses were applied on the same blood sample. The T lymphocytes apoptosis rate seems to respond in a linear way according to the irradiation dose (Gy) and according to the bleomycin concentration. (Data not shown).

Apoptosis rate model according to the irradiation (Gy):

$$y_i^{ir} = f_i^{ir}(x^{ir}) = \beta_0 + \beta_1 x^{ir} + b_{0i} + \epsilon_i \quad (1)$$

Apoptosis rate model according to the compound (µg/mL):

$$y_i^{co} = f_i^{co}(x^{co}) = \alpha_0 + \alpha_1 x^{co} + a_{0i} + \epsilon_i \quad (2)$$

The combination of the two models hereinabove allows determining a dose of bleomycin concentration ($\tilde{x}^{co}$) to be applied for mimicking the effect of an irradiation ($x^{ir}$):

$$\tilde{x}^{co} = \frac{\hat{\beta}_0 + x^{ir}\hat{\beta}_1 - \hat{\alpha}_0}{\hat{\alpha}_1}$$

Using RILA measures in 10 donors, it was possible to estimate the different parameters of this mathematic formula. The parameters obtained by such formula can be calculated for given duration of exposition and concentration of bleomycin.

$\hat{\beta}_0$ ranges from about 10 to about 20. This parameter corresponds to an apoptosis average value for irradiation level at zero.

$\hat{\beta}_1$ ranges from about 0.5 to about 2. This parameter corresponds to the slope, i.e., to the increase of apoptosis for each 1 Gy increase.

$\hat{\alpha}_0$ ranges from about 7.5 to about 20. This parameter corresponds to the apoptosis average value for bleomycin concentration at zero.

$\hat{\alpha}_1$ ranges from about 0.03 to about 0.15. This parameter corresponds to the slope, i.e., to the increase of apoptosis for each 1 µg/mL increase.

Bleomycin Concentration Validation

The Bleomycin concentration determined with the equation disclosed hereinabove was validated on 40 blood samples. For each blood samples, T lymphocytes apoptosis rate were obtained after an 8 Gy irradiation (RILA procedure disclosed above) or by treatment with 135-160 µg/mL of bleomycin, for a duration of exposition comprised between 65 and 75 hours (about 70-72 hours).

For a same donor, the apoptosis rates obtained by the two treatments were compared by calculating the coefficient of variation (CV). The CV between these 2 conditions were calculated according to the following formula: CV=(Standard deviation/Average apoptosis)×100.

The average CV for these 40 donors was 6.5%. This percentage was lower than 10%, which represents the experimental variation of the RILA assay.

These results were later reproduced on a larger (more than 100) number or donors.

It is also to be noted that the batch of bleomycin used for these experiments is different from the one tested above for the determination of the duration of exposure. Depending on the batch, a variation in the effective concentration can be observed and the effective concentration must be thus verified for any new batch of bleomycin used, in order to adjust the concentration. However, the duration of exposure must still remain higher than 50 hours.

These results thus show that it is possible to reproduce the apoptosis consequences of irradiation by using bleomycin as a radiomimetic, and that the contact of the radiomimetic shall be more than 50 hours.

The invention claimed is:

1. An in vitro method for mimicking the effect of an ionizing radiation on T cells of a subject, wherein said effect is the percentage of apoptosis of lymphocytes observed 48 hours after irradiation, comprising contacting the T cells of the subject with a concentration of bleomycin for a period of time of 50 hours to 75 hours, and measuring the T cells apoptosis percentage, wherein the T cells apoptosis percentage after contact with bleomycin corresponds to the apoptosis percentage of T cells 48 hours after being subjected to ionizing radiation, wherein the concentration of bleomycin ranges from about 100 µg/mL to about 300 µg/mL and wherein the method mimics the effect of an ionizing radiation at a dose ranging from about 2 Gy to about 10 Gy.

2. The in vitro method of claim 1, wherein the concentration of the bleomycin is determined using the following mathematic formula $$\tilde{x}^{co} = \frac{\hat{\beta}_0 + x^{ir}\hat{\beta}_1 - \hat{\alpha}_0}{\hat{\alpha}_1}$$

wherein ($\tilde{x}^{co}$) is the dose of compound to be applied for mimicking the effect of a specific irradiation dose ($x^{ir}$), $\hat{\beta}_0$ corresponds to an apoptosis average value for irradiation level at zero, $\hat{\beta}_1$ corresponds to the slope, i.e., to the increase of apoptosis for each 1 Gy increase, $\hat{\alpha}_0$ corresponds to the apoptosis average value for bleomycin concentration at zero and $\hat{\alpha}_1$ corresponds to the slope, i.e., to the increase of apoptosis for each 1 µg/mL increase.

3. The in vitro method of claim 1, wherein the T cells are contacted with bleomycin at a temperature of about 37° C. and in the presence of about 5% $CO_2$.

4. The in vitro method of claim 1, wherein the T cells are $CD8^+$ T cells.

5. The in vitro method of claim 1, wherein the T cells are comprised in a T cell containing sample selected from a blood sample, a sample recovered from bone marrow, lymph node tissue, cord blood, thymus tissue, tissue from a site of infection, ascites, pleural effusion, spleen tissue, and a tumor sample.

6. The in vitro method of claim 1, wherein the T cells contacted with bleomycin for a period of time of at least 50 hours are from a T cell containing sample previously obtained from the subject, and wherein the individual radio-sensitivity of the subject is determined.

7. The in vitro method of claim 6, wherein the subject is diagnosed with cancer.

8. The in vitro method of claim 6, wherein the subject is treated or is planned to be treated with an ionizing radiation treatment.

9. The in vitro method of claim 6, wherein the risk of developing side effects after an ionizing radiation treatment is also determined.

10. The in vitro method of claim 6, comprising:
  (a) contacting a T cell containing sample previously obtained from a subject with bleomycin, and
  (b) measuring CD8$^+$ T cell apoptosis in the sample from the subject.

11. The in vitro method of claim 1, wherein the method mimics the effect of a ionizing radiation at a dose of about 8 Gy.

12. The method of claim 5, wherein the T cell containing sample is a blood sample or a whole blood sample.

13. An in vitro method for mimicking the effect of an ionizing radiation at a dose of 8 Gy on T cells of a subject, wherein said effect is the percentage of apoptosis of lymphocytes observed 48 hours after irradiation, comprising contacting the T cells of the subject with a concentration of bleomycin for a period of time of 65 to 75 hours, and measuring the T cell apoptosis percentage, wherein the T cells apoptosis percentage after contact with bleomycin corresponds to the apoptosis percentage of T cells 48 hours after being subjected to the ionizing radiation, wherein the concentration of bleomycin ranges from about 135 µg/mL to about 160 µg/mL.

14. The in vitro method of claim 13, wherein bleomycin is applied for 70 to 72 hours.

* * * * *